United States Patent
Johnson et al.

(10) Patent No.: US 10,898,169 B1
(45) Date of Patent: Jan. 26, 2021

(54) SPUTUM COLLECTION AND WASHING APPARATUS AND A METHOD OF USING IT

(71) Applicant: Forward Industries, Inc., Hauppauge, NY (US)

(72) Inventors: Norman Eric Johnson, Big Bear City, CA (US); Karl Boldt, Blasdell, NY (US); Joseph Toro, East Patchogue, NY (US); Jason LeGoff, Miller Place, NY (US)

(73) Assignee: FORWARD INDUSTRIES, INC., Hauppauge, NY (US)

( * ) Notice: Subject to any disclaimer, the term of this patent is extended or adjusted under 35 U.S.C. 154(b) by 0 days.

(21) Appl. No.: 17/069,509

(22) Filed: Oct. 13, 2020

(51) Int. Cl.
*A61B 10/02* (2006.01)
*A61B 10/00* (2006.01)
*B01L 3/00* (2006.01)
*G01N 1/28* (2006.01)
*G01N 1/34* (2006.01)

(52) U.S. Cl.
CPC .......... *A61B 10/0051* (2013.01); *B01L 3/508* (2013.01); *G01N 1/286* (2013.01); *G01N 1/34* (2013.01); *B01L 2300/0609* (2013.01); *G01N 2001/2873* (2013.01)

(58) Field of Classification Search
None
See application file for complete search history.

(56) References Cited

U.S. PATENT DOCUMENTS

| | | | |
|---|---|---|---|
| 2,301,781 A | 11/1942 | Higbee | |
| 3,518,164 A | 6/1970 | Andelin | |
| 3,764,215 A | 10/1973 | Wallach | |
| 3,937,213 A | 2/1976 | McDonald | |
| 4,064,760 A | 12/1977 | Benjamin | |
| 5,897,840 A * | 4/1999 | Owens, Jr. ........... | A61B 10/007 220/505 |
| 9,113,850 B2 * | 8/2015 | Skakoon ............ | A61B 10/0051 |
| 2017/0196542 A1 * | 7/2017 | Spiteri .................... | A61J 19/02 |

FOREIGN PATENT DOCUMENTS

EP 0092914 A2 11/1983

\* cited by examiner

*Primary Examiner* — Paul S Hyun
(74) *Attorney, Agent, or Firm* — Koffsky Schwalb LLC

(57) ABSTRACT

A medical apparatus (FDA Classifications: "Sputum Specimen [In-Home] Self-Collection Device" and "In Vitro Medical Diagnostic Device") and method for self-collection, transport, decontamination and storage preservation of expectorated sputum specimens, to optimize specimen quality and reliability of clinical laboratory stain interpretation, culture and molecular diagnostic tests, thereby improving laboratory support for pathogen-specific treatment (antibiotic stewardship).

19 Claims, 18 Drawing Sheets

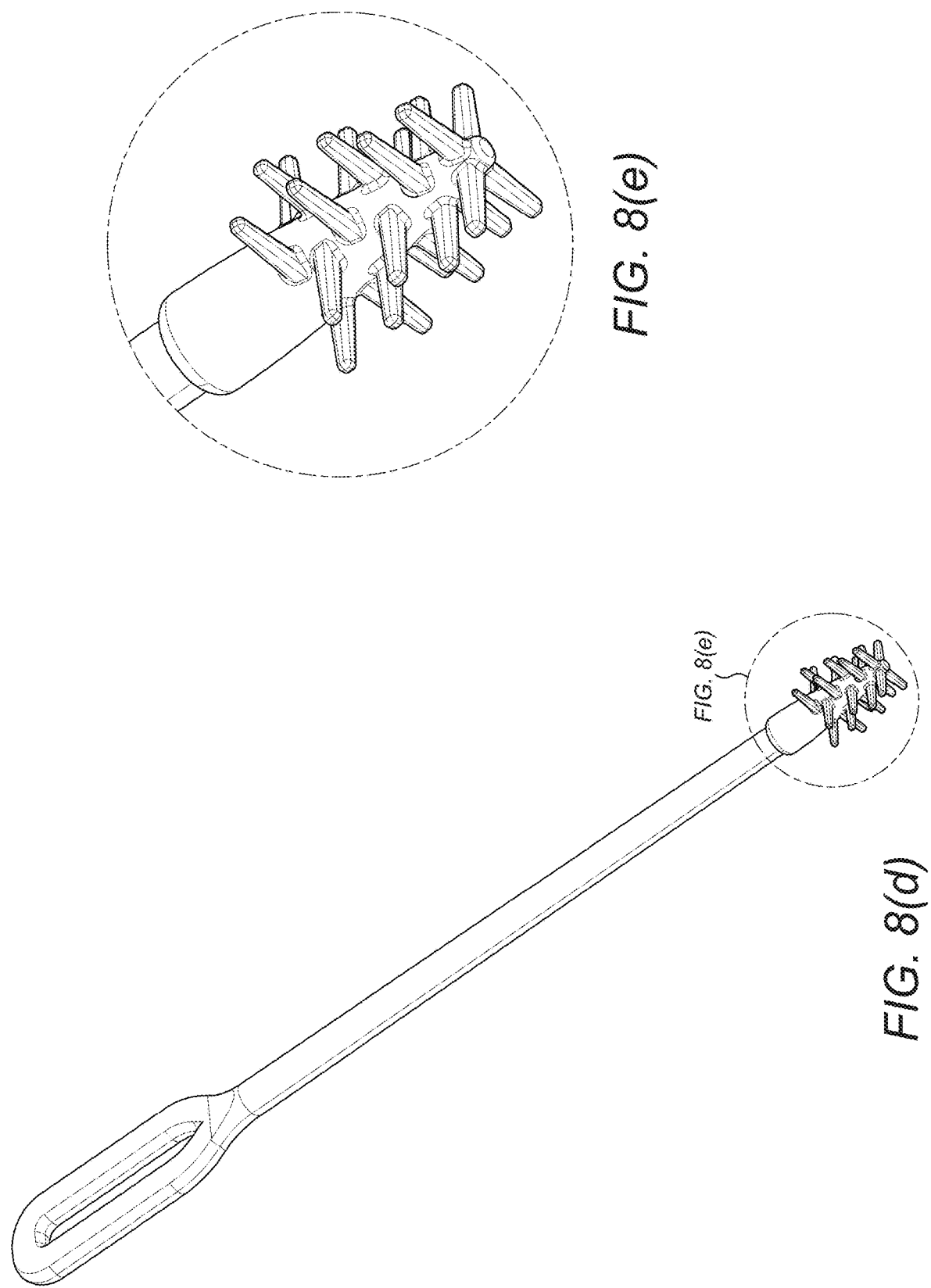

SPUTUM COLLECTION AND WASHING APPARATUS AND A METHOD OF USING IT

FIELD OF THE INVENTION

This medical invention is an apparatus (FDA classifications: "Sputum Specimen [In-Home] Self-Collection Device" and "In Vitro Medical Diagnostic Device") and method for self-collection, transport, decontamination, sampling and storage preservation of expectorated sputum specimens to optimize the accuracy of clinical diagnostic studies and thereby improve laboratory support for pathogen-specific treatment decisions (antibiotic stewardship). This "sputum-washing" invention is relevant to current worldwide public health emergencies including the COVID19 pandemic, tuberculosis, childhood pneumonia and microbial antibiotic resistance.

BACKGROUND OF THE INVENTION

Pulmonary infections threaten public health worldwide, and comprise a major portion of office visits, hospitalizations, morbidity, mortality, health care costs, work loss and antibiotic over-prescription generating microbial antibiotic resistance. During the current COVID-19 pandemic, millions have been sickened and hundreds of thousands killed by SARS-CoV-2 infection to date. Other millions annually suffer and die due to childhood pneumonia and tuberculosis. Appropriate therapy empowered by reliable identification of causative pathogens reduces morbidity, mortality, cost and risks of pathogen-blind (i.e., contra-indicated) antibiotic prescriptions.

One complacent yet widely-practiced "empiric" treatment for outpatient respiratory infections involves application of (pathogen-blind) "herd statistics" to individual outpatients, resulting in massive over-prescription of inappropriate antibiotics.

Appropriate therapy requires timely identification of the correct etiologic pathogen in every patient's case. Reliable sputum examination is the only way to directly identify lower respiratory pathogens, thereby empowering appropriate clinical treatment decisions (antibiotic stewardship).

One traditional laboratory method to identify respiratory pathogens is to "Gram stain" sputum (mucous secreted by bronchial epithelium "Goblet" cells) specimens. Sputum is normally sterile; Gram-staining infected "subglottic" (un-contaminated) sputum reliably identifies bacterial pathogens. However, subglottic sputum sampling requires invasive surgery (tracheal aspiration or intubation) and is therefore seldom used for outpatient specimen collection Gram stains are therefore most commonly performed on "expectorated" specimens (subglottic sputum coughed up and spit into a container.) Because the non-sterile oropharynx is normally colonized by extensive salivary microbial flora, the expectorated sputum bolus becomes contaminated as it passes through the mouth. Gram stain and culture of such contaminated (un-washed) specimens too often (up to 50%) fail to identify the obscured etiologic pathogen, leading many clinicians to view (unwashed) sputum studies as unreliable and therefor "irrelevant" to treatment decisions. Infectious disease consensus guidelines currently consider sputum studies "optional" for empirical treatment of outpatients, rather than optimal for pathogen-specific antibiotic stewardship Thus, contemporary treatment of outpatient pulmonary infection is pathogen-blind, encouraging antibiotic over-prescription, accelerating the phenomenon of microbial antibiotic resistance—currently a worldwide public health emergency.

"Decontaminated" sputum, from which salivary microbial flora has been removed, significantly improves laboratory stain, culture and molecular detection results. Salivary contaminants in expectorated specimen boluses are water-soluble; sputum is not. "Washing" an expectorated sputum bolus with water or saline dilutes and removes these soluble contaminants, improving specimen test quality ("Bartlett criteria"). Sensitivity and specificity of all diagnostic studies are improved by sputum-washing: even currently-rejected (unwashed) boluses are transformed into "Bartlett quality" (average<<10 SEC/LPF) specimens for reliable testing.

Prior "sputum-washing" art has not been embraced by clinical practice. Manual research techniques (e.g., stirring a bolus in water; tea-strainers) have not evolved into an acceptable practice for over 125 years. This invention apparatus and method is designed to facilitate user-friendly self-collection, transport, pre-assay decontamination, sampling and storage preservation of expectorated sputum bolus specimens One object of this invention is to facilitate self-collection of expectorated sputum specimens by outpatients, without need for inpatient "medical supervision". This apparatus is user-friendly for patients, with a wide-mouth target, textured ergonomic grip surface and secure, non-leaking screw-top lid with write-on identification label surface. Safe-distancing from others during expectoration can be accomplished with simple illustrated patient instructions. Any concern that "unsupervised" sputum collection might lower specimen quality is fully mitigated by washing (decontaminating) expectorated boluses with this invention before testing. Because outpatients (with a licensed provider requisition) may submit specimens prior to their appointment, "unsupervised self-collection" of expectorated sputum specimens empowers pathogen-specific antibiotic stewardship for outpatients, needed to reverse the single greatest cause (pathogen-blind empiric antibiotic over-prescription for outpatient respiratory infections) of the current worldwide microbial antibiotic resistance emergency.

It is also an object of this invention to provide secure enclosure of potentially bio-hazardous sputum specimens for transport from point of self-collection to point of clinical testing, and for subsequent storage. This GMP-compliant apparatus design is leak-proof and breakage-resistant. It is compatible with 6-inch pneumatic transport systems. Decontamination and refrigerated storage preserves specimen quality in the same multi-functional device used for self-collection and transport.

It is also an object of this invention to provide an apparatus that facilitates reliable, timely, cost-effective removal of oropharyngeal contaminants from expectorated sputum bolus specimens, by washing them in water or saline.

It is also an object of this invention to improve specimen sampling for clinical diagnostic studies, including stains, cultures and molecular (nucleic acid) detection. A specially designed sputum-adherent "grabber" brush tool (hereafter referred to as "grabber tool") is incorporated for user-friendly washed specimen sampling from the loop plate at the apex of the cone mesh. A mucous "cutter" groove is incorporated into the "sputum retention barrier" to facilitate down-sizing "grabbed" specimen samples, if needed. Compared to traditional "microbial loops", the grabber tool also improves uniformity of specimen application (spreading) onto microscope slides.

It is also an object of this invention method to preserve expectorated sputum specimen quality for storage and further testing. The contaminant microbes in saliva reproduce at an exponential rate, as often as every 20 minutes. For this reason, expectorated sputum quality (by Bartlett criteria) degrades rapidly over time. It is recommended that expectorated bolus specimens be washed as soon as possible to remove contaminating salivary microbes before they reproduce. Decontaminated specimens can then be studied, and/or stored for follow-up testing (and/or re-washing), as indicated.

It is therefore an object of this invention design to improve cost-effectiveness of diagnostic sputum testing by optimizing expectorated specimen self-collection, transport, decontamination, sampling, and storage preservation within a single user-friendly, multifunctional apparatus/device.

Sputum studies, which this invention optimize, must be requisitioned by licensed clinical providers in most health care systems (e.g., Medicare). It is also an object of this invention to empower a medical practice paradigm-shift away from pathogen-blind "empiric" treatment of outpatient respiratory infections, by empowering pathogen-specific antibiotic stewardship. Such a paradigm shift is indicated for successful resolution of 4 current worldwide public health emergencies In the following description, the invented apparatus, including all its various embodiments, is referred to as a "sputum-washer": and the invented method is referred to as a "sputum washing."

SUMMARY OF THE INVENTION

Disclosed is a medical apparatus (which may be qualified under FDA classifications: "Sputum Specimen [In-Home] Self-Collection Device" and "In Vitro Medical Diagnostic Device") and method for self-collection, transport, decontamination, sampling and storage preservation of expectorated sputum specimens, to optimize reliability of clinical diagnostic testing, thereby improving laboratory support for pathogen-specific treatment decisions (antibiotic stewardship)

In one embodiment, the invented sputum-washer includes a transparent container with an opening at the top end, a mesh assembly situated within the container and above the container's bottom end, and a removable lid for sealable engagement with the top end of the container. The mesh assembly includes a mesh flange (mesh retainer) that is connected to the mesh and couples it to the container's sidewall. The flange includes a decanting port, located between the mesh and the container's sidewall, for enabling drainage of a wash fluid out of the container opening after washing.

In one embodiment, the invented method includes collecting the sputum specimen into the mesh zone, filling the container up to a fill line with a saliva-dissolving wash fluid (such as saline or tap water), sealing the container with a removable lid to create a watertight seal, agitating the sputum sample in the container for a predetermined duration (about 5 seconds), removing the lid, and draining the wash fluid from the opening at the top of the container via the decanting port of the mesh assembly.

In another alternative embodiment, the sputum-washer includes two openings (one at the top of the container and one at the bottom), two removable lids (top and bottom lids), and a mesh cone assembly without a decanting port.

In another alternative embodiment, the sputum-washer includes two openings (one at the top of the container and one at the bottom) ("dual-openings sputum washer"), a mesh cone assembly without a decanting port, and three removable lids (two alternate lids for sealing the container from the top, and one lid for sealing it from the bottom). One of the top lids incorporates suction ports.

For example, in one embodiment, the invented apparatus comprises: (a) a container having a top end, a bottom end, a peripheral sidewall, and an opening at the top end; (b) a mesh cone positioned within the container opening and above the bottom end, the mesh cone configured to support a sputum specimen and further configured to allow passage of a wash fluid: (c) a flange supporting the mesh and coupling it to the peripheral sidewall of the container, the flange having a decanting port located between the mesh and the peripheral sidewall; and (d) a removable lid configured to seal the container opening, wherein the flange and the removable lid are configured to form a (sputum retention) barrier between the mesh and the decanting port, the barrier capable of blocking the sputum specimen from passing through it during washing and wash-decanting. The peripheral sidewall may include a wash-fluid fill line ("wash line").

The removable lid may be secured to the container via a threaded connection. A lower surface of the removable lid includes a first circumferential rib, such that the above (sputum retention) barrier is created when the rib presses against the flange. The lower surface of said removable lid may comprise a second circumferential rib having a larger diameter than the first circumferential rib, the second circumferential rib configured to enhance sealing of the container when the second circumferential rib presses against the flange.

The flange may further comprise an overhang above the mesh, the overhang configured to prevent discarding of the sputum specimen during draining of the wash fluid via the decanting port and out of the container opening, which is located at the top of the container. The edge of the overhang has a V-shaped profile that facilitates cutting (limiting sample size) of the washed specimen during removal from the mesh cone loop plate.

The invented sputum washer may further comprise a grabber tool to enable manual removal (sampling) of the washed specimen from the loop plate. The grabber tool is configured for stowing in the decanting port within the container wash area.

In one embodiment of the invention, the mesh is cone-shaped and comprises a sampling plate ("loop plate") at the apex of the cone, or it may replace the mesh material at the apex of the cone altogether.

In one alternative embodiment of the invention, the sputum-washer apparatus comprises (a) a container having a top end with a first opening, a bottom end with a second opening, and a peripheral sidewall between the top end and the bottom end; (b) a mesh cone positioned within the container and above the bottom end, the mesh cone configured to support up to a predetermined amount (e.g., 30 cc) of expectorated sputum specimen bolus and further configured to allow passage of wash fluid, the mesh cone further comprising a sampling, or "loop plate": (c) a flange supporting the mesh and coupling it to the peripheral sidewall; (d) a first removable lid configured to create a watertight seal at said first opening following deposition of the sputum specimen bolus into the mesh zone: and (e) a second removable lid configured to create a watertight seal at the second opening, and further configured to be removed for drainage of the wash fluid out of the container through the second opening, wherein said apparatus provides for washing of the specimen and draining of the wash fluid.

The invention also includes a novel method for self-collection, transport, decontamination, sampling, and storage of washed sputum specimens. For example, in one embodiment, the method comprises the steps of:
(a) providing an apparatus that includes
   (i) a container having a top end, a bottom end, a peripheral sidewall, and an opening at the top end; (ii) a mesh cone positioned within the opening and above the bottom end, the mesh cone configured to retain a sputum specimen and further configured to allow passage of a wash fluid; (iii) a flange supporting the mesh and coupling it to the peripheral sidewall, the flange having a decanting port located between the mesh cone and the peripheral sidewall; and (iv) a removable lid;
(b) depositing the sputum specimen in the mesh zone (i.e., on the mesh or on a sampling plate at the bottom of the mesh); (c) sealing the container using the removable lid, wherein the flange and the removable lid cooperate to form a barrier between the mesh and the decanting port (at the upper surface of the flange), the barrier capable of restraining the specimen from passing through it;
(d) agitating the specimen in the presence of the wash fluid to dilute and dissolve contaminants from the specimen bolus; (e) unsealing said container; and (f) draining the wash fluid from the container via the decanting port and out of the container opening. In the invented method, the agitating, or tumbling, step may be performed for a predetermined duration (e.g., approximately 5 seconds).

The invented method may further comprise a step, upon arrival in the lab and after removing the lid, of removing the grabber tool from its stowed position through the decanting port.

The invented method may further comprise the step of using a grabber tool to manually sample (remove a portion of) the washed specimen from the mesh cone loop plate in the container. The method may further include downsizing a sample by dragging it through the cutting groove on the specimen retention barrier of the flange.

BRIEF DESCRIPTION OF THE FIGURES

The accompanying figures, where like reference numerals refer to identical or functionally similar elements throughout the separate views, together with the detailed description below, are incorporated in, form part of the specification, and serve to further illustrate embodiments of concepts that include the claimed invention and explain various principles and advantages of those embodiments.

FIGS. 8(a)-8(e) are detailed views of an embodiment of the grabber tool of the invented sputum-washer.

Figure 1:
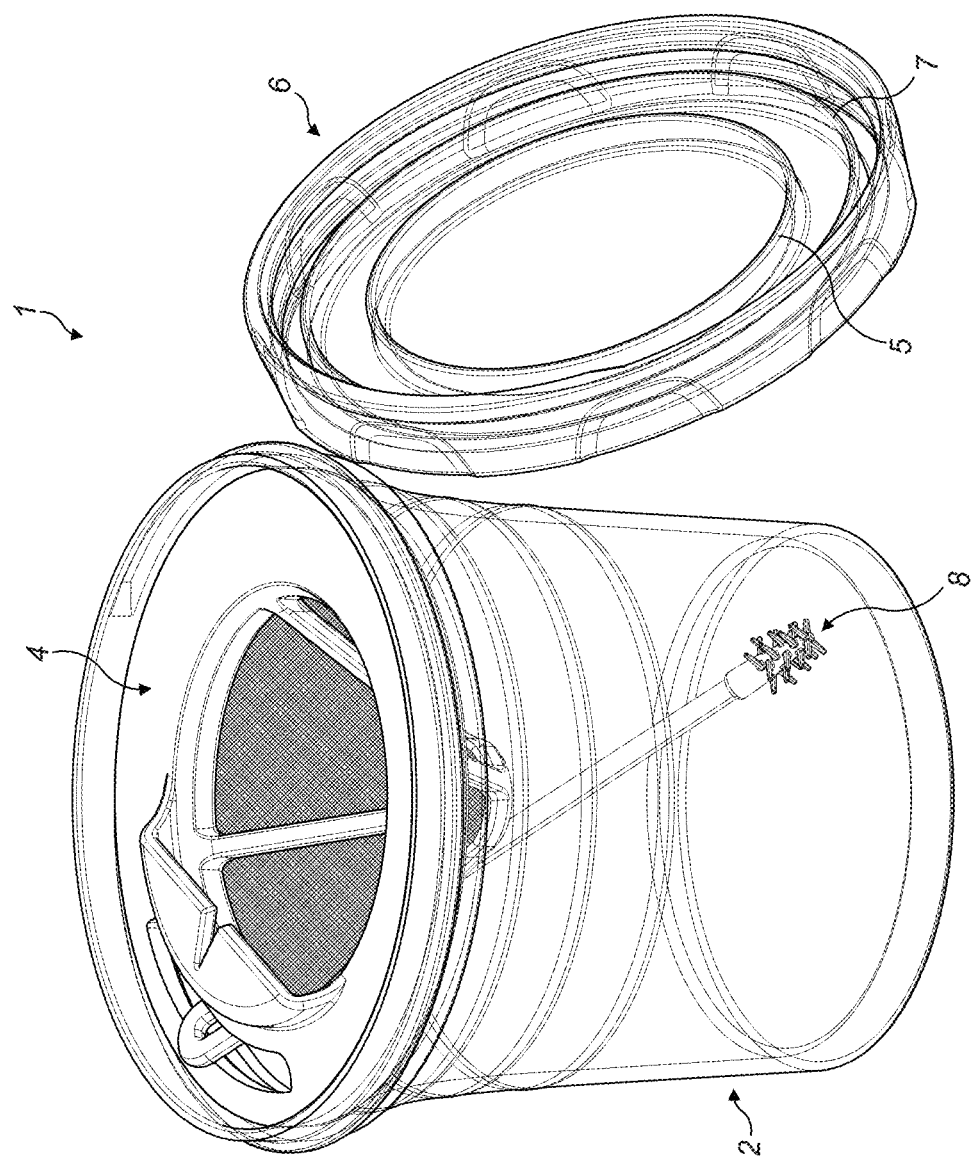
FIG. 1 illustrates an embodiment of the present sputum-washer apparatus invention.

Skilled artisans will appreciate that elements in the figures are illustrated for simplicity and clarity and have not necessarily been drawn to scale. For example, the dimensions of some of the elements in the figures may be exaggerated relative to other elements to help improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

The following detailed description discloses some embodiments of sputum collection and washing apparatus ("sputum-washer") of the present invention and method of using it.

FIG. 1 illustrates an embodiment of a disposable sputum-washer device of the present invention. The illustrated sputum-washer 1 includes a transparent container 2, a mesh cone assembly 4 situated within the container, and a removable lid 6. In addition to having a threaded sidewall inside the outer periphery (ridge) of the lid, for sealable engagement with the threads on the exterior at the upper edge of the container's sidewall, the lower surface of the lid includes two circumferentially extending ridges, an inner rib 5 and an outer rib 7, the functions of which are explained with reference to FIG. 3. FIG. 1 also shows a grabber tool 8 stowed inside the sputum-washer 1. A grabber tool 8, the purpose of which is described further below, is depicted as a component of the sputum-washer apparatus 1. Its purpose is to facilitate sampling, however, the grabber tool is not essential for collection of, or washing, the specimen using the invented sputum-washer.

Figure 2:
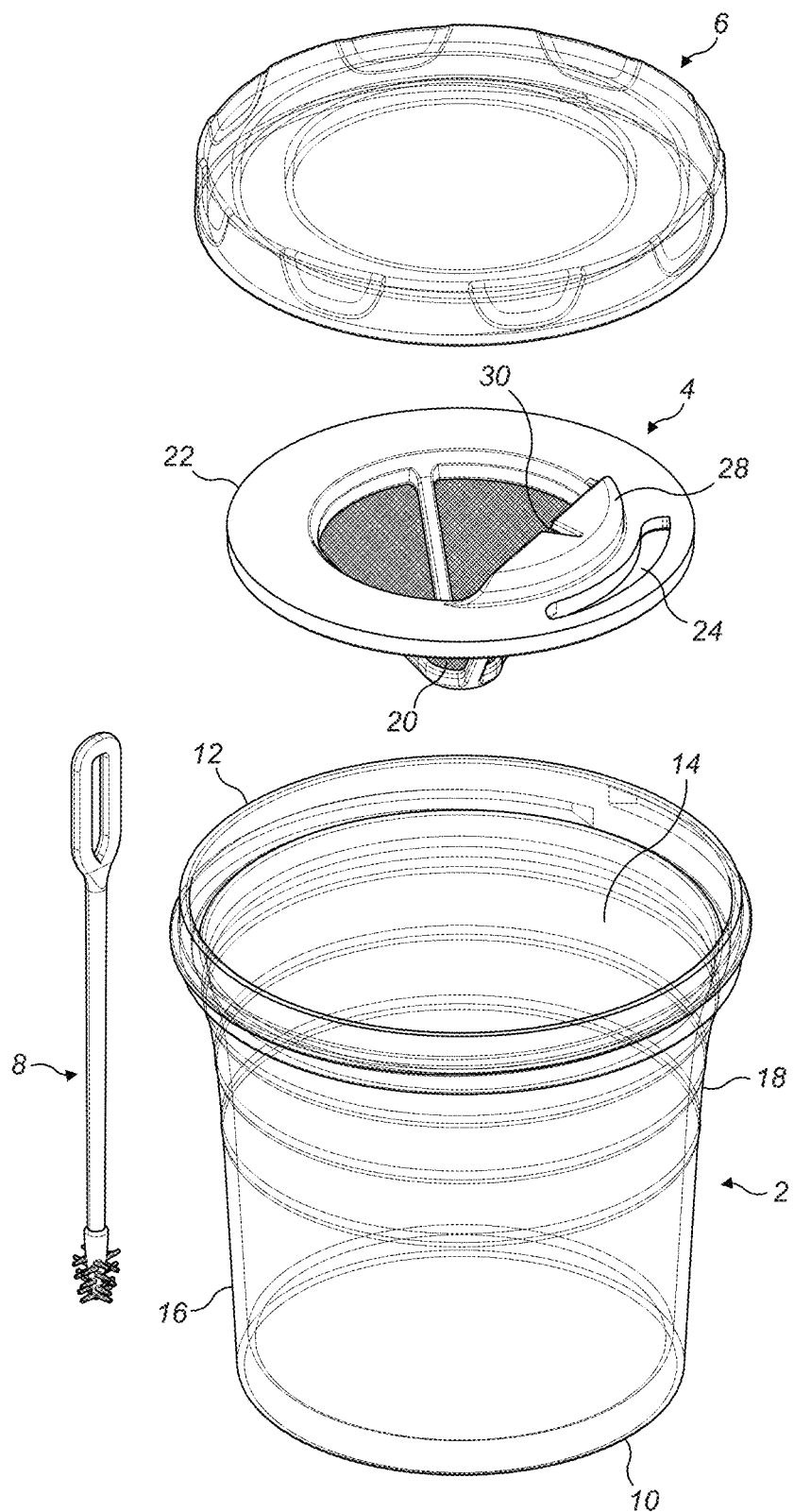
FIG. 2 illustrates an exploded view of the apparatus in FIG. 1.

FIG. 2 depicts an exploded view of the sputum-washer of FIG. 1, disclosing the above described components in more detail. For example, the container 2 includes a bottom end 10, a top end 12 with an opening 14 therein, and a peripheral sidewall 16. The peripheral sidewall includes a fill line (wash line) 18, the purpose of which is explained further below. The mesh cone assembly 4 gets seated, e.g., snapped-in, within the container opening 14, such that it rests on or against a lip or ridge on an interior surface of the peripheral sidewall 16. As a result, when the mesh cone assembly 4 is seated in the container 2, it creates a sputum collecting zone in the container. In an alternative embodiment, the mesh cone assembly 4 may be coupled to the interior of the container (by welding or an adhesive).

In the embodiment depicted in FIG. 2, the mesh assembly 4 comprises a cone-shaped mesh 20 that is supported in the container opening 14 by a mesh-retaining flange ("flange") 22 and is positioned above the bottom end 10 of the container. The mesh cone, which is configured to support a sputum specimen, includes perforations that are sized to substantially prevent sputum from passing through (due to its viscosity), while allowing a wash fluid, e.g., saline or tap water, to pass through them. The mesh is wash fluid-permeable while being relatively sputum-impermeable. The flange 22 helps to retain and to secure (or couple) the mesh 20 in the container. The flange 22 further includes a decanting port 24 that facilitates draining (decanting) of the wash fluid out of the container. Although in the embodiment in FIG. 2, the mesh 20 and the flange 22 are shown as being integrally connected, the invention is not so limited and may have these components as separate elements.

FIG. 2 further illustrates the flange 22 including an overhang 28 above the mesh 20. The overhang creates a barrier to retain the sputum specimen in the mesh area during decanting, thus preventing accidental loss of the specimen. The edge of the overhang 28 includes a feature that facilitates cutting (limiting the size) of the washed specimen during removal from the loop plate. In the embodiment shown in FIG. 2, the feature is a V-shaped groove 30.

FIG. 2 further illustrates the removable lid 6. In the preferred embodiment of the sputum washer of FIG. 2, the removable lid 6 includes a threaded sidewall for engaging a set of threads on the exterior surface of the container's sidewall 16, to create a watertight seal between the lid and the container. While the embodiment of FIG. 2 depicts threads as the lid-container connecting mechanism for creating the watertight seal, the invention is not so limited, and contemplates creation of the seal by other means, e.g., snap fit, pressure fit, etc.

FIG. 2 also illustrates a stowed grabber tool 8, designed to facilitate sampling (removal of a portion) of the sputum specimen from the mesh or loop plate surface. The grabber tool includes a brush at its lower end and a proximal handle extending therefrom. This way, a controlled portion of the washed sputum specimen can be manually removed from the invented sputum-washer for laboratory analysis.

In one embodiment of the present invention, the container 2, as well as the lid 6, is made out of a transparent material, such as plastic or glass, with a fill line and other indicators, such as user instructions, molded or extruded therein. Transparency of the container and the lid enhances the overall usability of sputum washer device and contents. In other embodiments, however, container and/or the lid could also be made from other materials, such as metal. While the embodiment of FIG. 2 shows the container 2 as having a substantially cylindrical shape, the invention is not so limited and other shapes, rectangular, etc. could be used.

Figure 3:
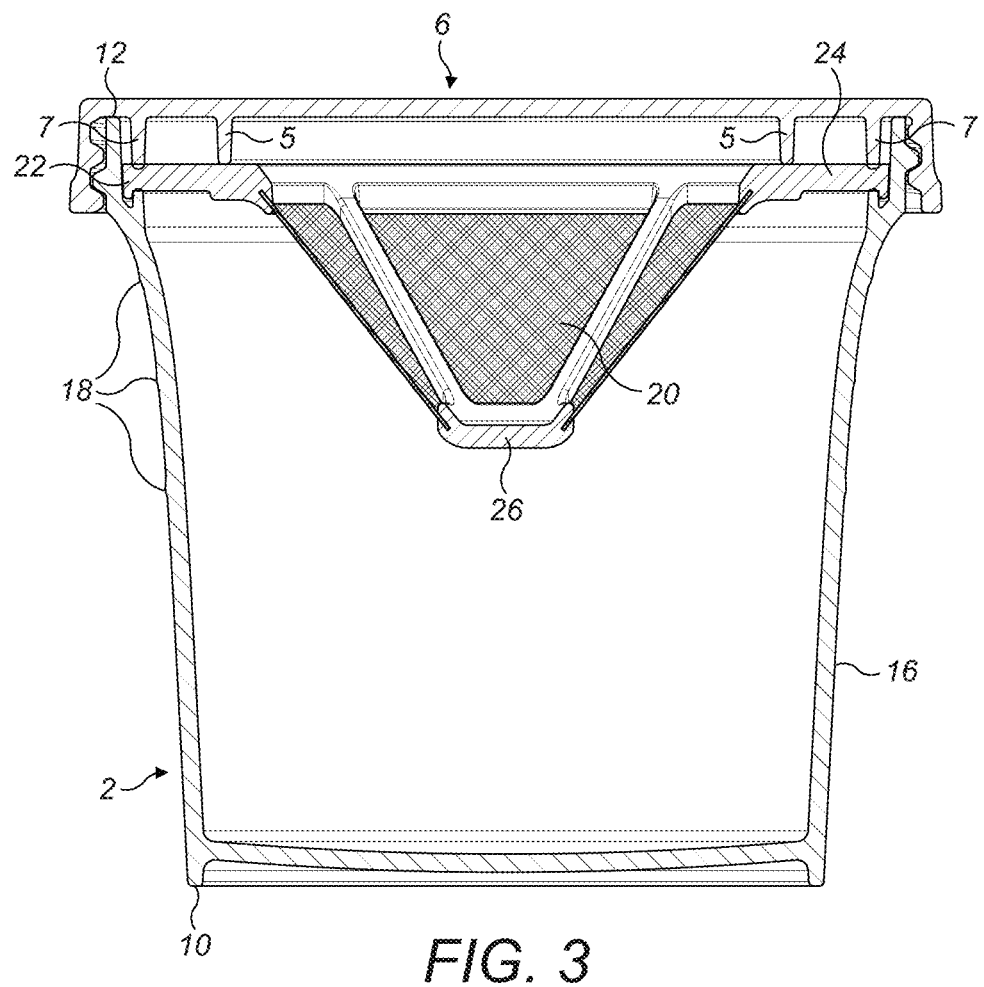
FIG. 3 is a cross-sectional view of the invented apparatus.

FIG. 3 is a cross-sectional view of the apparatus in FIG. 1, but with the removable lid 6 shown in a sealed engagement with the container 2. Application of the removable lid 6 creates additional internal structures of the invented sputum-washer. For example, in addition to providing a watertight sealing of the container, FIG. 2 shows the lid's circumferential internal ribs 5 and 7 engaging the flange 22 on both sides of the flange's decanting port 24, the internal rib 5 engaging the flange 22 further away from the container's peripheral sidewall 16 than the internal rib 7. Although both internal ribs 5 and 7 help to retain the flange 22, and its coupled mesh 20, during washing, the two internal ribs 5 and 7 serve additional purposes.

For example, the circumferential inner rib 5 is used to create a sputum-specimen retention barrier over the flange 22, between the mesh 20 and the decanting port 24. Specifically, FIG. 3 shows the rib 5 contacting and pressing against the upper surface of the flange 22, between the mesh 20 and the decanting port 24. In the preferred embodiment, the flange is made of a deformable material, which facilitates creation of the specimen-retention barrier. Because the lid 6 and the flange 22 are each water impermeable, the inner rib 5 and the flange 22 cooperate to create a fluid barrier that prevents fluid transfer (sputum and wash fluid) between the decanting port and the mesh over the upper surface of the flange 22 during washing of the sputum. While in a preferred embodiment of the invention the barrier formed by the inner rib 5 and the flange 22 is water impermeable, it is sufficient for the present invention for the barrier to be merely sputum-impermeable. Thus, having the internal rib that is merely sputum-impermeable will suffice to form the disclosed barrier. (Note, regardless of the material used for the internal rib 5, the removable lid 6 and flange 22 are water impermeable.)

While in the depicted embodiment, the barrier is formed by the lid's interior rib 5 pressing from the top on the flat upper surface of the flange 22, any cooperation between the upper surface of the flange 22 and the lower surface of the lid that creates the barrier will suffice. For example, instead of being a part of the lid 6, the interior rib 5 could be a structure extending upward from the upper surface of the flange 22, thus contacting/pressing against the lid at the lid's lower surface. In another embodiment, the sputum-retention barrier may be formed by a structure where an interior rib of the lid is engaged by a cooperating structure extending upward from the top surface of the flange and engaging the lid's rib anywhere (vertically) in between the lid and the flange.

The circumferential inner rib 7 is also shown as contacting, or pressing, against the flange 22. When the flange is made of a soft durometer deformable (malleable) material, the rib 7 creates a further watertight seal, in addition to any seal created by the threaded lid-container connection, for the invented sputum washer.

The above described components create an arrangement in which a sputum specimen, deposited onto the mesh, is retained in the mesh area of a sealed container during washing of the specimen with a wash fluid.

Figure 4C:
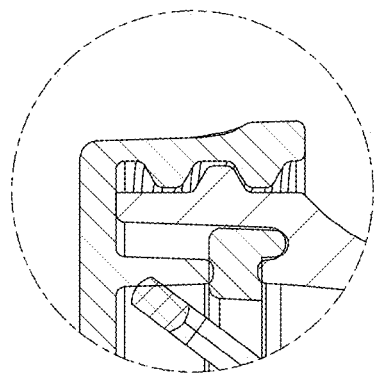
FIGS. 4 (a)-4(c) depict an embodiment of the invented sputum-washer with additional detail.
Figure 4B:
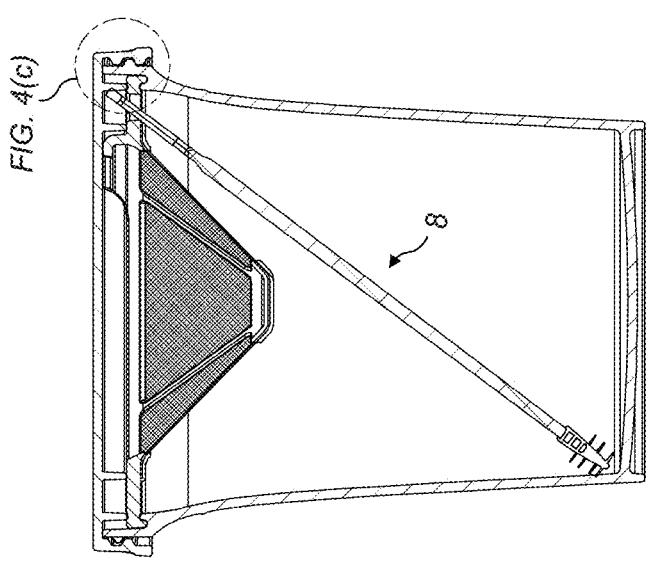
Figure 4A:
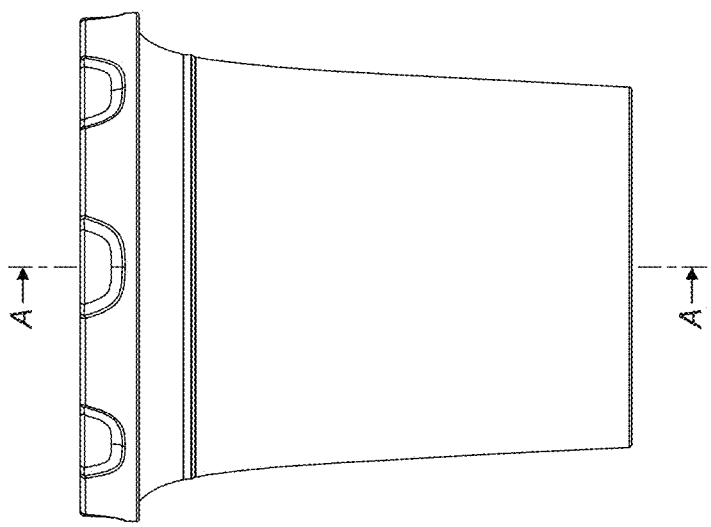

FIGS. 4(a) through 4(c) depict an embodiment of the invented sputum-washer with additional detail views. For example, FIG. 4(a) is a side view of the sputum washer with the lid on. FIG. 4(b) depicts a cross-sectional view of the sputum washer along the line "A-A" in FIG. 4(a). The cross-sectional view of FIG. 4(b) differs from the cross-sectional view in FIG. 3 in that it further shows the grabber tool 8 in a stowed position inside the container, with the top end of the tool protruding from the decanting port 24. FIG. 4(c) is a magnified view of the area "B" of FIG. 4(b). For example, FIG. 4(c) depicts the top end of the grabber tool 8 passing through the decanting port 24 and resting against the circumferential interior rib 7 of the lid 6.

Figure 5B:
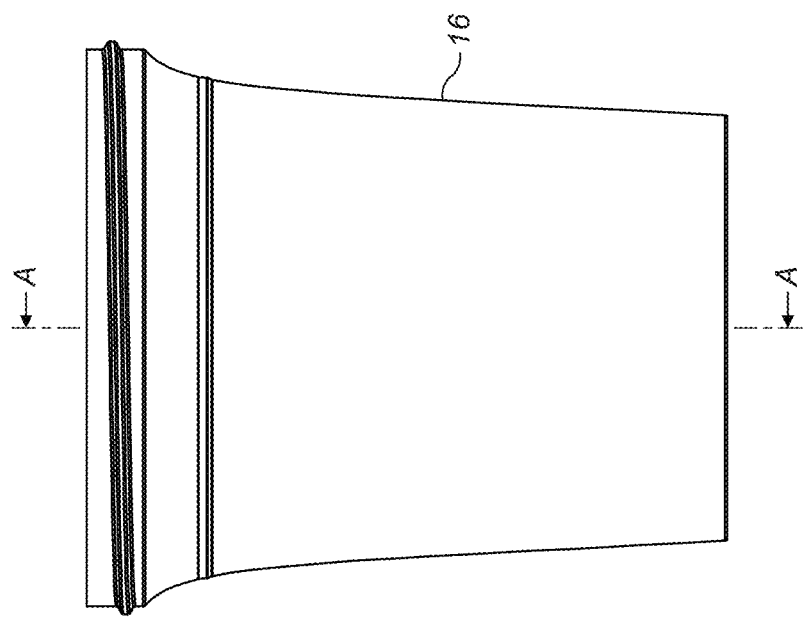
FIGS. 5(a)-5(e) are detailed views of an embodiment of the container of the invented sputum-washer.
Figure 5A:
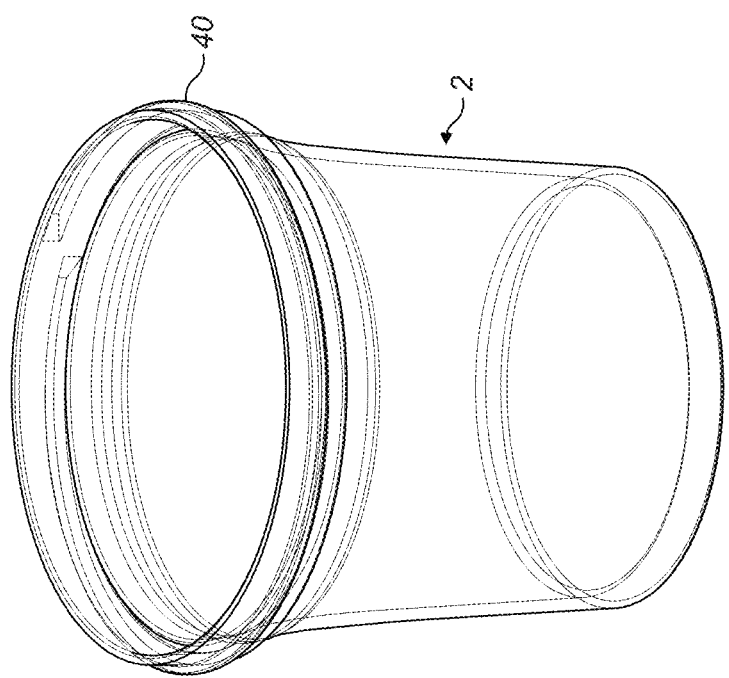
Figure 5C:
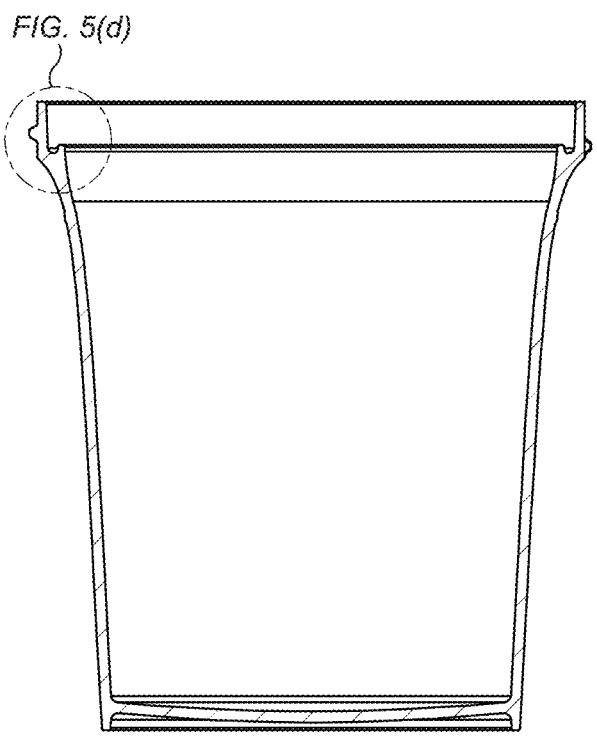
Figure 5D:
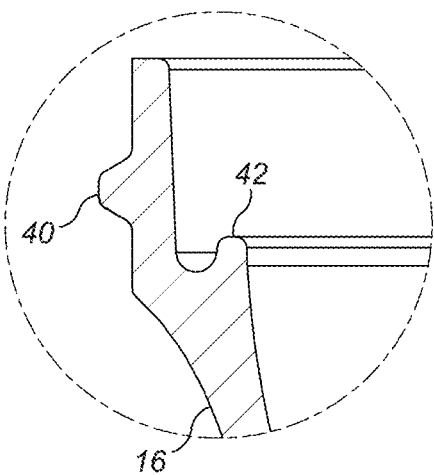
Figure 5E:
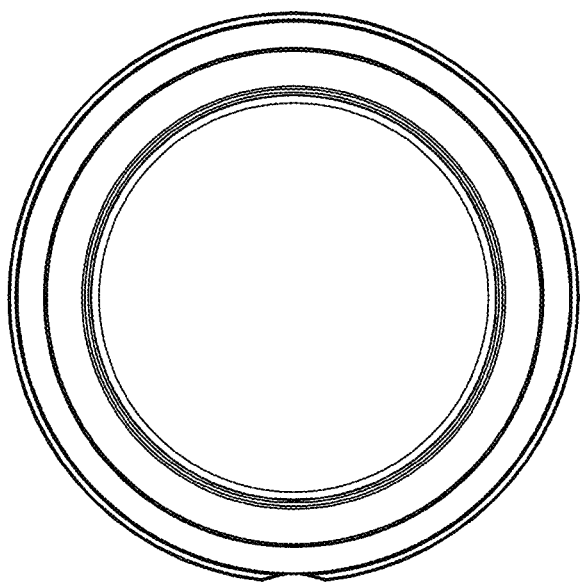

FIGS. 5(a)-5(e) illustrate the container 2 in further detail. FIG. 5(a) is a perspective view of the container, which in the preferred embodiment is formed from a transparent material, such as glass or plastic. The container has a generally cylindrical shape with threads 40 located at the top of the exterior side wall 16. FIG. 5(b) is a side view of the container in FIG. 5(a), showing a slight flaring of the exterior sidewall 16 at the top. FIG. 5(c) is a cross-sectional view of the container in FIG. 5(b) along the line "A-A." The sidewall 16 as well as the bottom of the container are shown as having a certain thickness and profile. FIG. 5(d) is a magnified view of the exterior sidewall 16 in area "B" of FIG. 5(c). For example, FIG. 5(d) shows a thread 40 on the outer surface of the exterior sidewall 16, and a lip (protrusion) 42 on the inner surface of the sidewall 16 for supporting the flange 22 of the mesh assembly 4.

Figure 6A:
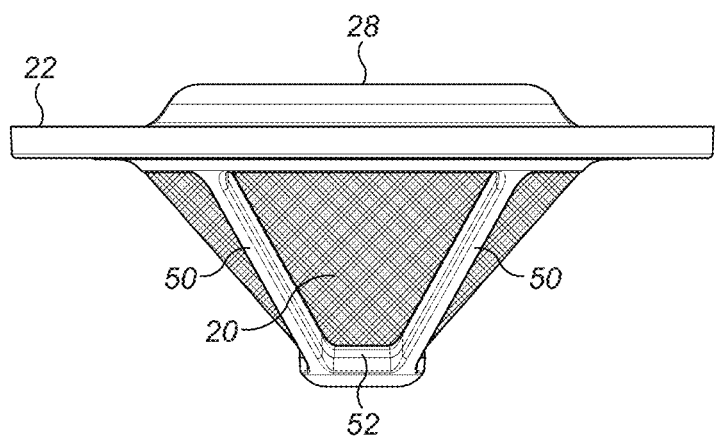
FIGS. 6(a)-6(e) are detailed views of an embodiment of the mesh cone assembly with apical sampling plate of the invented sputum-washer.
Figure 6B:
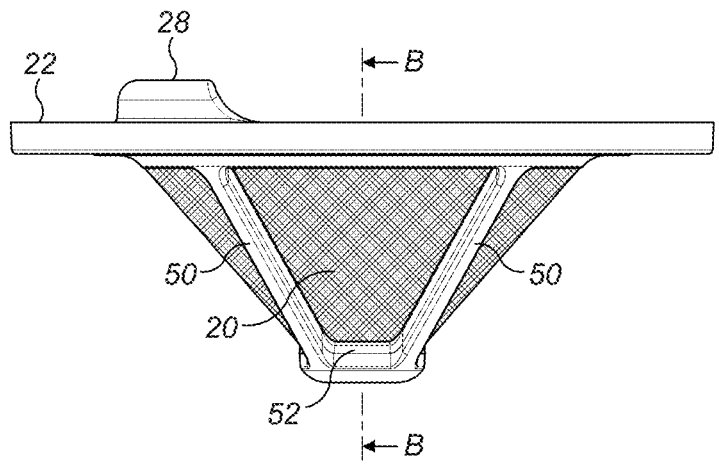

FIGS. 6(a)-6(e) are detailed views of a preferred embodiment of the mesh cone assembly 4. FIG. 6(a) is a front view of the mesh assembly. It illustrates the mesh 20 extending below the flange 22 and the mesh overhang 28, which in the preferred embodiment also extends up from the flat portion of the flange 22. The flange is further shown to include downwardly converging projections for supporting the mesh 20 from underneath, allowing the mesh to form a cone. The invention contemplates the mesh being made out of plastic, nylon, stainless steel, or other materials. In an alternative embodiment, the mesh can be made out of perforated rigid or semi-rigid materials. At the bottom, the mesh cone assembly includes a sampling loop plate 52 for supporting a sputum specimen as it slides down the mesh wall following deposition upon it. FIG. 6(b) is a side view of the mesh assembly of FIG. 6(a), providing a detailed view of the overhang 28.

Figure 6C:
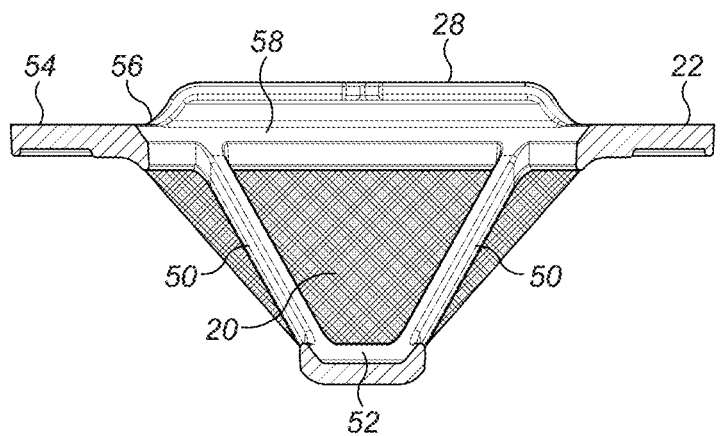

FIG. 6(c) is a cross-sectional view of mesh assembly 4 along the line "A-A" in FIG. 6(b). The flange 22 is shown having a body 58 (either plastic or metal) with an over-molded section 54 along the edge. The over-molded portion of the flange is made of a soft durometer (malleable) material (soft plastic or rubber) that cooperates with the ribs 5 and 7 of the lid 6 to form a retention barrier and a watertight seal as discussed above. In addition to the over-mold 54, the flange 22 may include an over-mold insert seal 56.

Figure 6D:
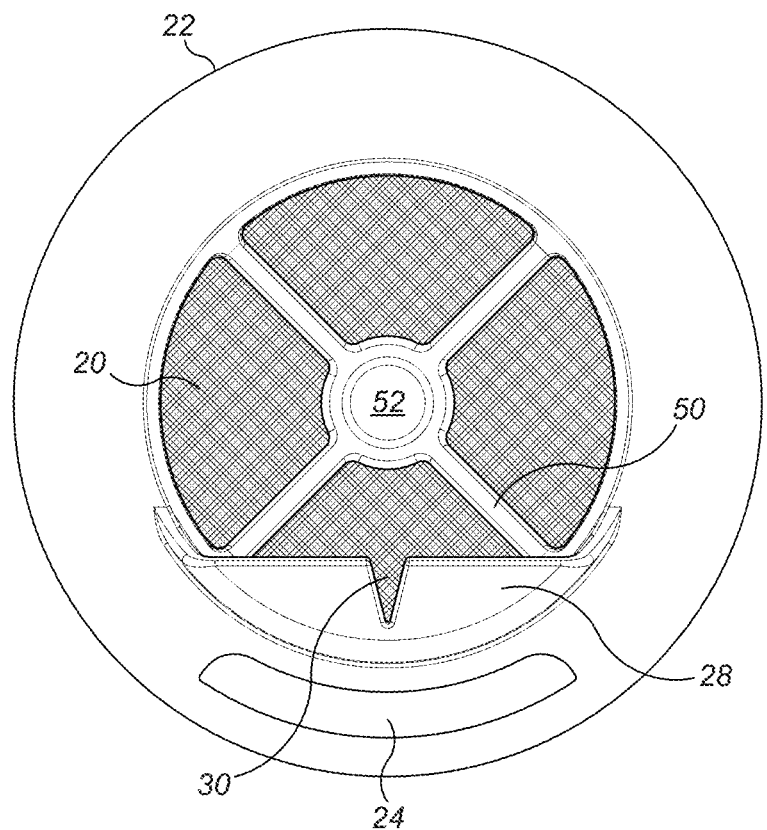
Figure 6E:
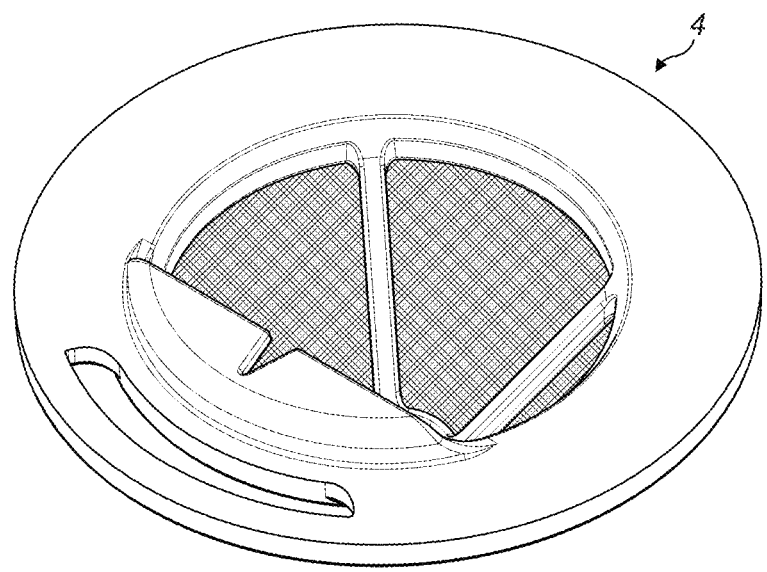

FIG. 6(d) represents a top view of the mesh cone assembly. In addition to the mesh assembly components discussed in references to FIGS. 6(a)-6(c), FIG. 6(d) also shows the decanting port 24 and the sputum-cutter V-groove 30. FIG. 6(e) is a perspective of the mesh assembly 4, showing the components of the mesh cone assembly from a different angle.

Figure 7A:
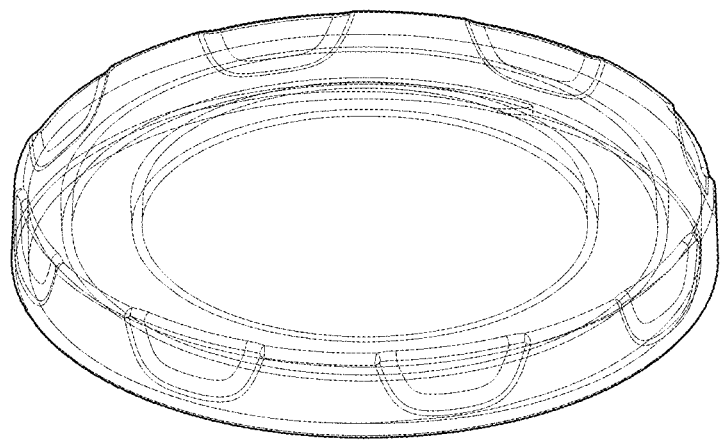
FIGS. 7(a)-7(e) are detailed views of an embodiment of the removable lid of the invented sputum-washer.
Figure 7B:
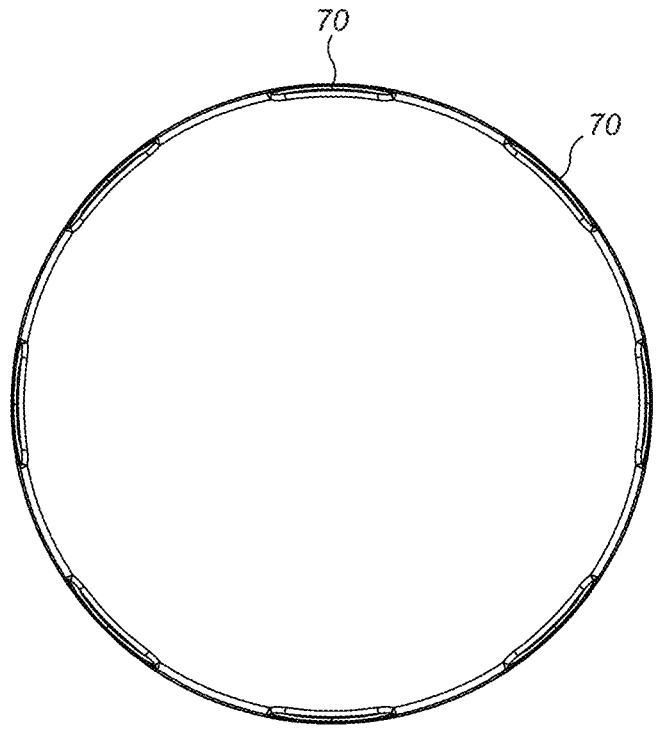
Figure 7C:
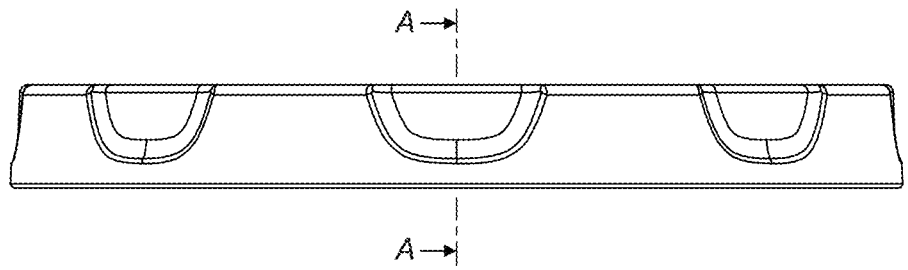
Figure 7D:
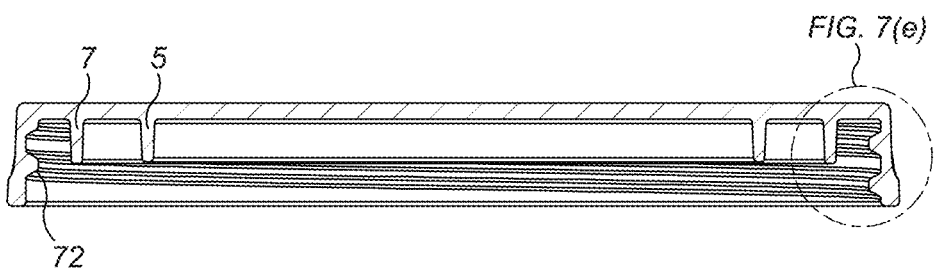

FIGS. 7(a)-7(e) are more detailed views of the removable lid 6 of the invented sputum-washer from different angles. FIG. 7(b) provides a top view of the lid. Reference numeral 70 represents areas along the outer surface of the lid with a textured surface, for better manual grip when opening and closing the lid. FIG. 7(c) is a side view of the removable lid in FIG. 7(a), depicting the lid's intermittently textured areas from the side. FIG. 7(d) is a cross-sectional view of the lid along the line "A-A" in FIG. 7(c). It shows the lid's threaded sidewall 72 and its circumferential internal ribs 5 and 7, described above.

Figure 7E:
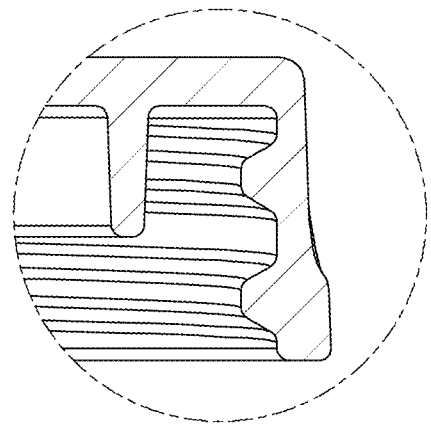

FIG. 7(e) is a magnified view of the lid in area "B" of FIG. 7(d)). For example, FIG. 7(e) shows the internal rib 7 and a thread feature of the lid's sidewall.

Figure 8A:
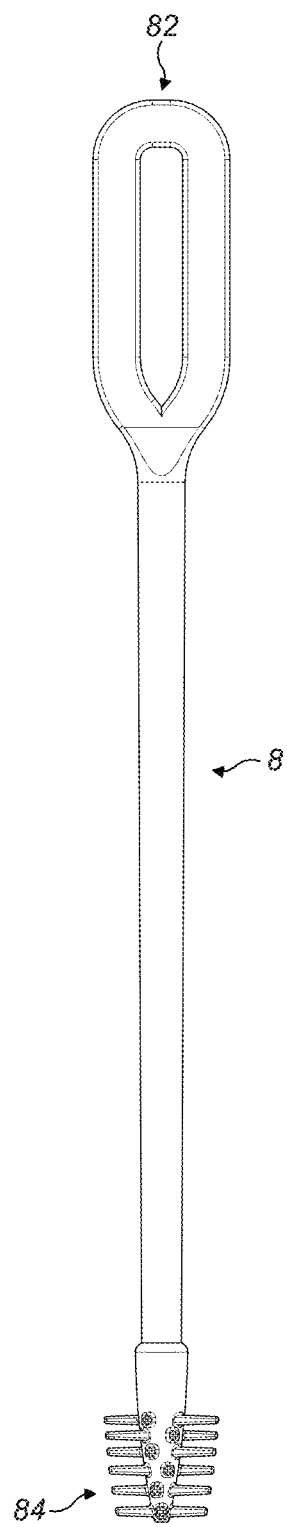
Figure 8B:
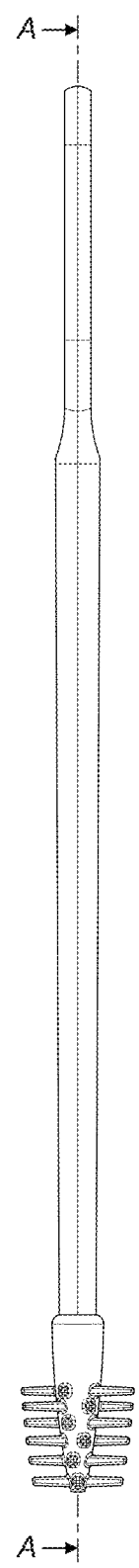
Figure 8C:
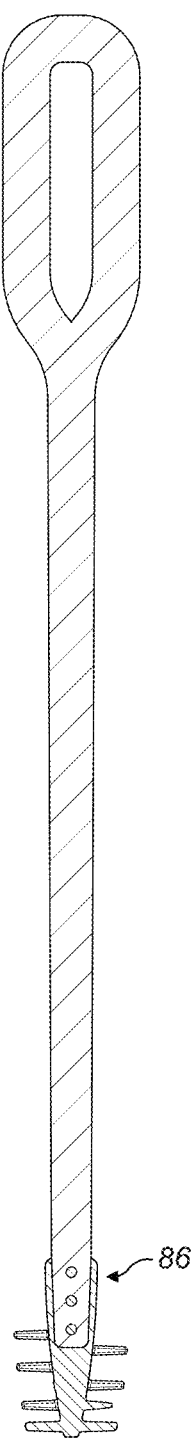

FIGS. 8(a)-8(e) provide detailed views of the grabber tool 8. As shown in FIG. 8(a), grabber tool 8 has an eyelet 82 at its top end and a plurality of spikes, or brush 84 at the bottom ("tip") end. Although in one preferred embodiment, the body of the grabber tool is formed from plastic, the invention contemplates the body of the grabber being formed from other materials, such as glass, metal, etc. In the preferred embodiment, the tip end further includes a silicon over-mold. FIG. 8(b) depicts the grabber tool of FIG. 8(a) rotated 90 degrees. FIG. 8(c) is a cross-sectional view of the grabber tool along the line "A-A" in FIG. 8(b), showing an over-mold capture feature 86. FIG. 8(d) is a perspective view of the grabber tool 8, and FIG. 8(e) is a detailed view of the tip end of the grabber tool in FIG. 8(d), showing the brush (spikes) and the over-mold in more detail.

Figure 9:
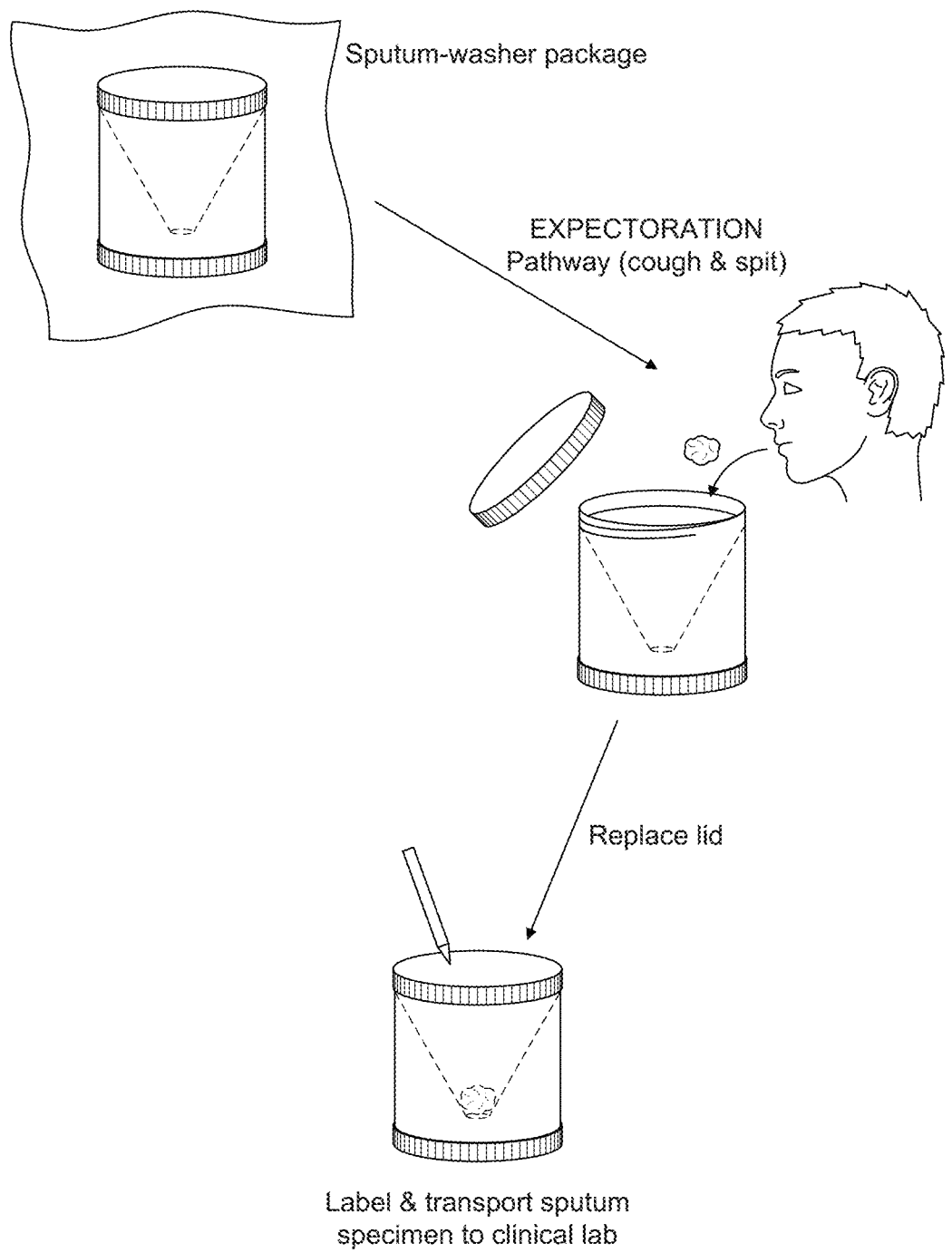
FIG. 9 discloses an embodiment of the expectoration self-collection method of the present invention.
Figure 10:
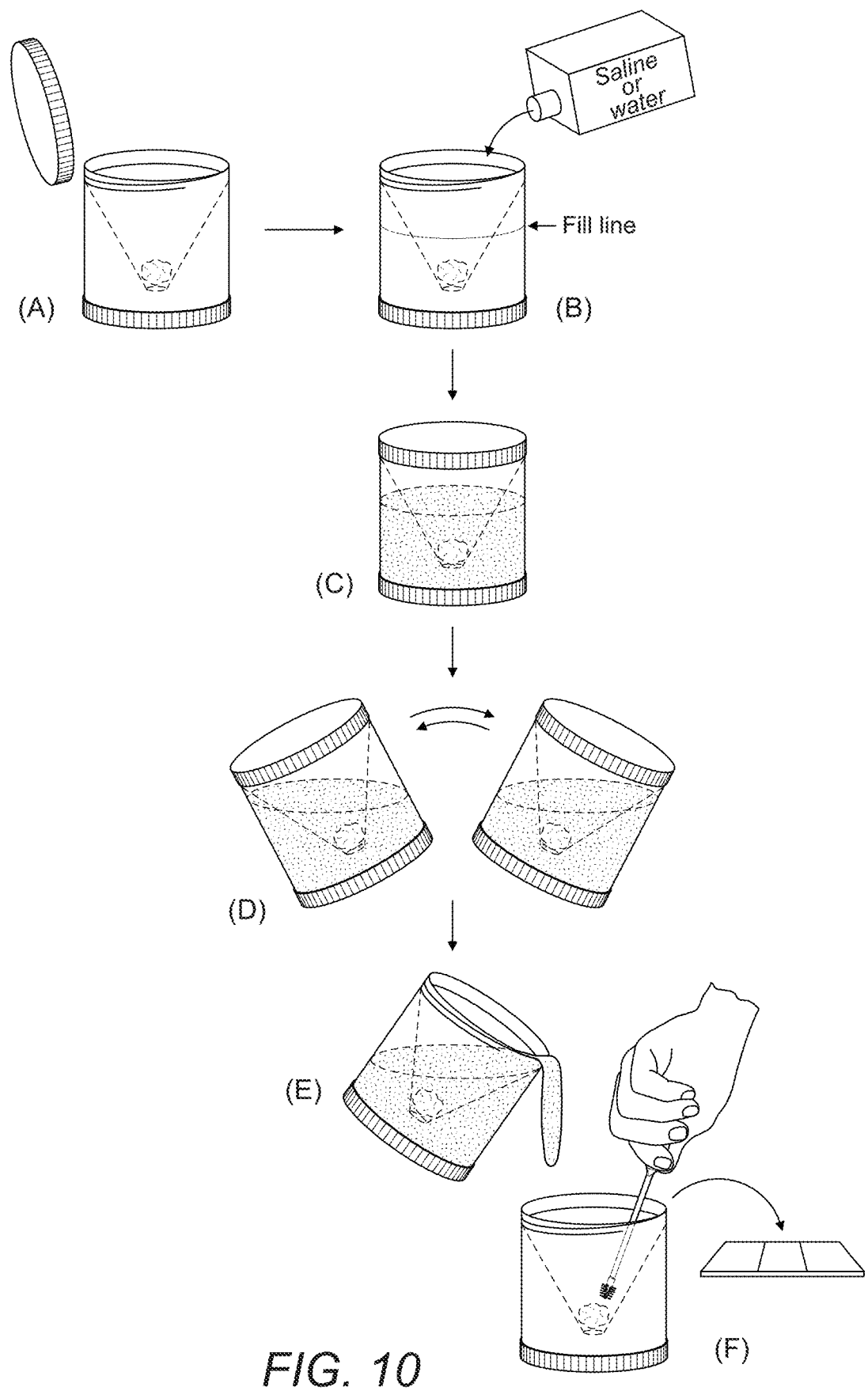
FIG. 10 discloses an embodiment of a sputum-washing method of the present invention.

FIGS. 9 and 10 illustrate sputum collection and washing methods of the present invention using the single-lid sputum-washer disclosed in FIGS. 1-7 above. For example, FIG. 9 illustrates "expectorated" specimen collection and FIG. 10 illustrates sputum specimen washing with the invented single-lid sputum-washer.

The sputum self-collection method illustrated in FIG. 9, can be performed by the patients themselves, with or without "medical supervision." The optimal collection time is after waking up and before eating. Because the sputum-washer device may come in a sterile, sealed package (see the image at the top of FIG. 9), the expectorated collection process starts with opening the package and removing the sputum-washer device from it. The next step is to remove the lid 6 off the sputum-washer (the grabber tool 8 should remain stowed in the decanting port during specimen collection and transport.). The outpatient will "blow" their nose and rinse out their mouth with tap water, then breathe deeply and cough up sputum from deep in the chest, then spitting it (about 5 cc) into the wide-mouth sputum-washer collection device. Expectoration may be stimulated with hypertonic saline nebulization and/or postural percussion for "medically-supervised" inpatients (see the image in the middle of FIG. 9). The next steps are to replace the lid 6 back onto the container 2, to label the sputum-washer with the patient's name, date, and time, and to transport the specimen to a clinical lab as quickly as possible (see the image at the bottom of FIG. 9). Should there be any delay in transporting the specimen to the lab, the specimen should be refrigerated.

FIG. 10 illustrates the sputum-washing method of the present invention using the single-lid sputum-washer disclosed above (in a CLA-certified clinical laboratory under a bio-hazardous hood with universal infection precautions). The sputum-washing process in FIG. 10 starts with removal of the lid 6 from the container (see illustration (A) in FIG. 10). Remove the grabber tool from the decanting port. The next step is to fill the container with a saliva-dissolving wash fluid, e.g., water or saline, up to a fill line 18 (see illustration (B) in FIG. 10). The next step is to replace the lid 6, thereby sealing the sputum specimen and the wash fluid within the device (see illustration (C) in FIG. 10). The device is then manually tumbled/rolled (i.e., agitated) for a predetermined duration (e.g., approximately 5 seconds) to expose the sputum bolus to the wash fluid, in order to dilute and dissolve the salivary contaminants from the specimen bolus (see illustration (D) in FIG. 10). In the next step of the invented method, the lid 6 is removed and the wash fluid, containing dissolved contaminants, is poured out of the decanting port 24 and out of the opening 14 at the top of 2 (see illustration (E) in FIG. 10). Once the sputum specimen has been washed, the specimen can be sampled from the mesh or loop plate using the grabber tool, for Gram stain (Bartlett quality check) or other diagnostic testing procedure (see illustration (F) in FIG. 10). The specimen could also be placed into a petri dish, for growing and testing of cultures, or in a test tube for molecular testing.

Moreover, the sputum cutting feature of invented sputum washer (which in the preferred embodiment is located on the flange overhang but could be located at another location on the flange, or on the container itself) may be used to cut, or limit, the specimen (downsize the sample adhering to the grabber brush). Alternatively, sampling of the washed sputum specimen can proceed from the plate with a loop or pipet.

Traditionally, a Gram stain "Bartlett score" is performed to evaluate sputum quality for diagnostic testing. In the preferred embodiment, if the score is greater than 10 buccal SEC/HPF average in 25 selected LP fields, the specimen is rejected for testing. However the sputum-washing procedure invented herein "rescues" (improves Bartlett score of) such contaminated (low quality) boluses, transforming them into reliable specimens for study (rather than current practice of discarding them with lab request for a better, repeat specimen). Once the washed specimen has been decontaminated, it may be sampled or refrigerated for future testing. Depending on storage duration (usually about 5 days), the washing procedure may be repeated later. When the specimen is no longer needed, the sputum-washer device may be disposed of, according to CLIA bio-hazardous waste management protocol.

Figure 11:
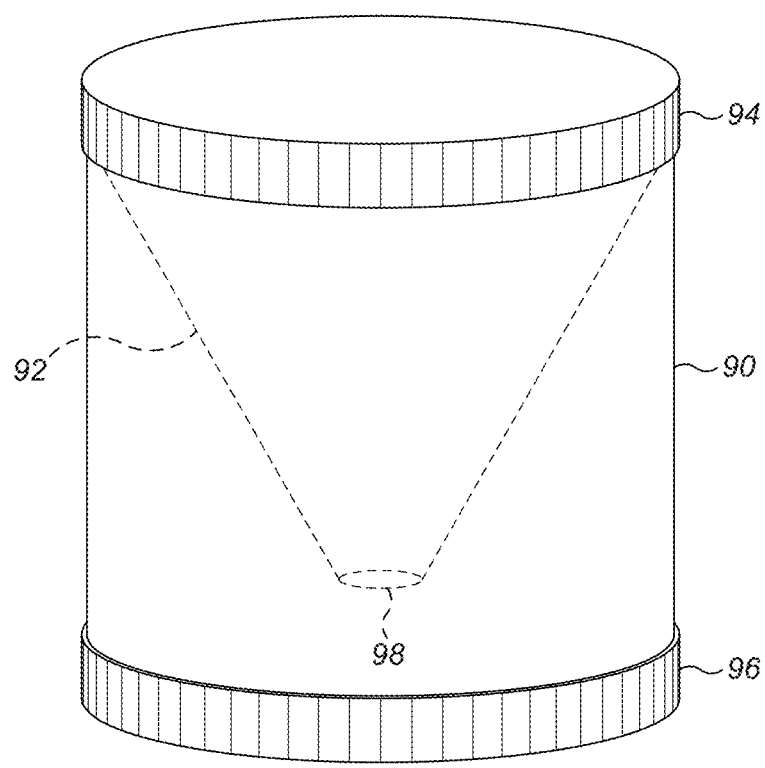
FIG. 11 discloses a second embodiment of the invented apparatus.

FIG. 11 illustrates an alternate embodiment of the invented sputum washer. Similar to the sputum washer disclosed in FIGS. 1-8, the sputum washer in FIG. 11 also comprises a container 90, a mesh assembly 92 situated within the container, and a removable lid 94 at the top of the container. However, unlike the container embodiment in FIGS. 1-8, which includes an opening at the container's top end only, the container 90 also includes an opening at its bottom end, for draining the wash fluid. As a result, the sputum washer embodiment in FIG. 11 not only includes a removable lid 94 at the top of the device ("top lid"), but also includes a removable lid 96 at the bottom ("bottom lid"). The fact that the bottom lid 96 can be removed, allows simultaneous washing of the sputum specimen and discarding of the wash fluid through the bottom opening of the container. The mesh assembly 92 of the sputum washer in FIG. 11 also partially differs from the mesh assembly 4 in FIGS. 1-8, in which wash fluid is drained/decanted from the top opening of the container. As a result, while including a mesh component similar to the mesh disclosed in the embodiment in FIGS. 1-8, a flange of the mesh assembly 92 need not include a decanting port 24 or an overhang 28 of the sputum washer of FIGS. 1-8. As a result, the flange of the mesh assembly 92 can have a very simple and inexpensive design, whose purpose is to merely couple and secure the mesh component to the interior of the container 90. The container 90, similarly to the container disclosed in FIGS. 1-8, includes an internal lip or ridge to accept and secure the mesh assembly 92, such as by a snap-in or other type of attachment mechanism. Similar to the mesh assembly disclosed in FIGS. 1-8, the mesh assembly 92 may also include a plate, referred to in the art as a "loop plate" for specimen sampling at the bottom of the mesh. In comparison to prior art, the dual-cap sputum-washer embodiment in FIG. 11 simplifies overall design, enhances reliability, and reduces specimen rejection rates, cost and results time. An objective of this self-collection sputum-washer invention is to empower outpatient pathogen-specific antibiotic stewardship by reliably identifying causative pathogens prior to "time of service," when provider treatment decisions are made. For instance: a provider may order washed sputum testing at the time an outpatient schedules an appointment for "fever and cough" symptoms, with results available by appointment date. This will require provider education and motivation (standard-of-care paradigm shift) to prefer pathogen-identification over empiric (pathogen-blind) methods for treating outpatient respiratory infections.

Figure 12:
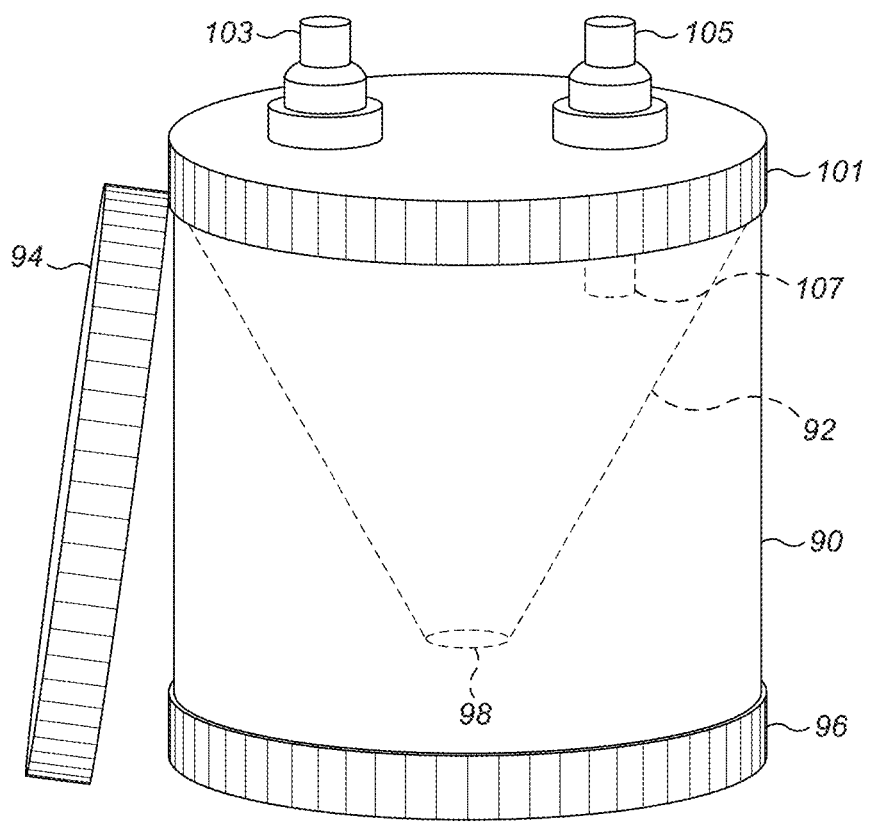
FIG. 12 discloses a third embodiment of the invented apparatus.

FIG. 12 depicts a modified embodiment of the invented sputum-washer apparatus of FIG. 11. In particular, the sputum-washer of FIG. 12 differs from the embodiment in FIG. 11 in that, in addition to the removable top lid 94, it also includes a second removable top lid 101, hereinafter referred to as "non-suction-top lid" and "suction-top lid," respectively. Unlike the non-suction-top lid 94, the suction-top lid 101 incorporates two suction ports: a vacuum port 103 and a patient-suction port 105. The patient suction port 105 may extend (107) below the inner surface of the suction-top lid which, once the suction-top lid is applied (screwed on, snapped on, etc.) to the container 90, the extension 107 would extend into the interior of the container 90, above the mesh cone. Inclusion of the "suction-top" lid 101 as an optional component of the sputum-washer allows for an alternative (vacuum suction-facilitated) methods of sputum collection, simplifying device design over the prior art and serving multiple specimen collection scenarios, embodied in FIG. 11.

Figure 13:
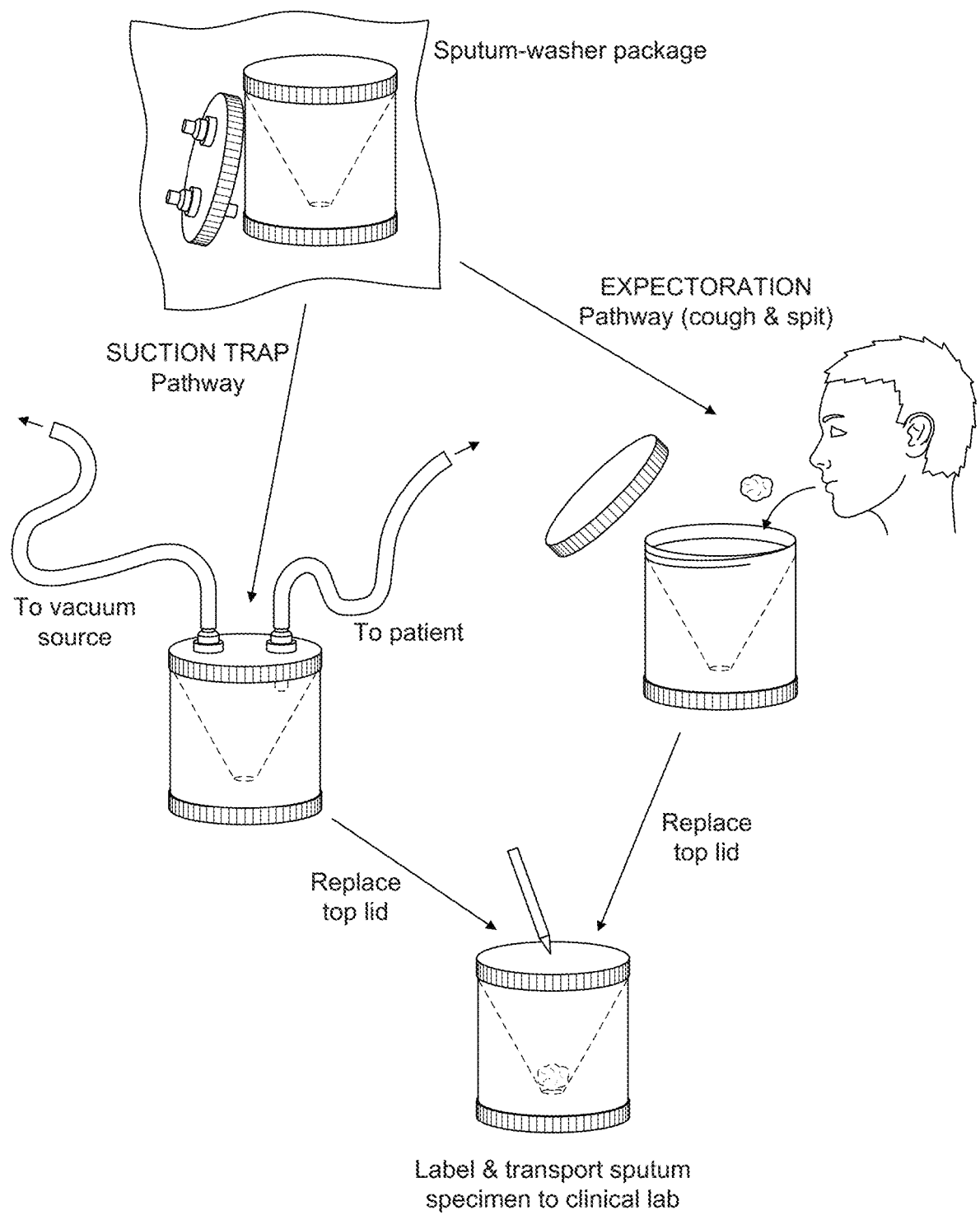
FIG. 13 discloses two alternative sputum collection methods of the present invention.

The sputum-washer embodiments of FIGS. 11 and 12 allow for different methods of sputum specimen collection and washing. FIG. 13 illustrates this difference in the context of specimen collection.

As disclosed in FIG. 13, specimen collection may be accomplished via two different pathways: an "expectoration" pathway for self-collection, shown on the right of FIG. 13, and a medically-supervised "suction trap" pathway on the left of FIG. 13. While the sputum-washer embodiment of FIG. 11 can only be used in the "expectoration" pathway, the sputum washer embodiment of FIG. 12 can be used in either pathway. The "expectoration" pathway in FIG. 13 is similar to the "expectoration" pathway described in FIG. 9.

The "suction trap" pathway, however, differs from the "expectoration" pathway in the number of steps. As shown on the left side of FIG. 13, the "suction trap" pathway also starts by opening the package comprising the sputum washer of FIG. 12. If the sputum-washer comes with the "non-suction-top lid" 94 applied, the lid 94 is removed but retained. Instead, the suction-top lid 101 is attached to the container top. Next, a vacuum suction source tubing is attached to the suction port 103 of the lid 101. Catheter, trocar, or scope tubing is attached to the patient port 105 of lid 101. This is illustrated in the middle of the left side in FIG. 13. Next, the patient is suctioned (per clinical protocol) to obtain and deposit sputum onto the mesh 92 of the device. Next, the suction-top lid 101 is removed and discarded, while the non-suction top lid 94 is reapplied to the container 90. Next, the sputum-washer (i.e., specimen) is labeled with the patient's name, date, and time. The specimen should be transported to a clinical lab as quickly as possible (see the image at the bottom of FIG. 13). (Vacuum-source tubing, patient-attaching tubing, and label are optional components of the invented sputum-washer.) If the grabber tool 8 was previously removed from the package, it may be placed into the container prior to closing the lid and labeling the specimen. Should there be any delay in transporting the specimen to the lab, the specimen may be refrigerated in the device.

Figure 14:
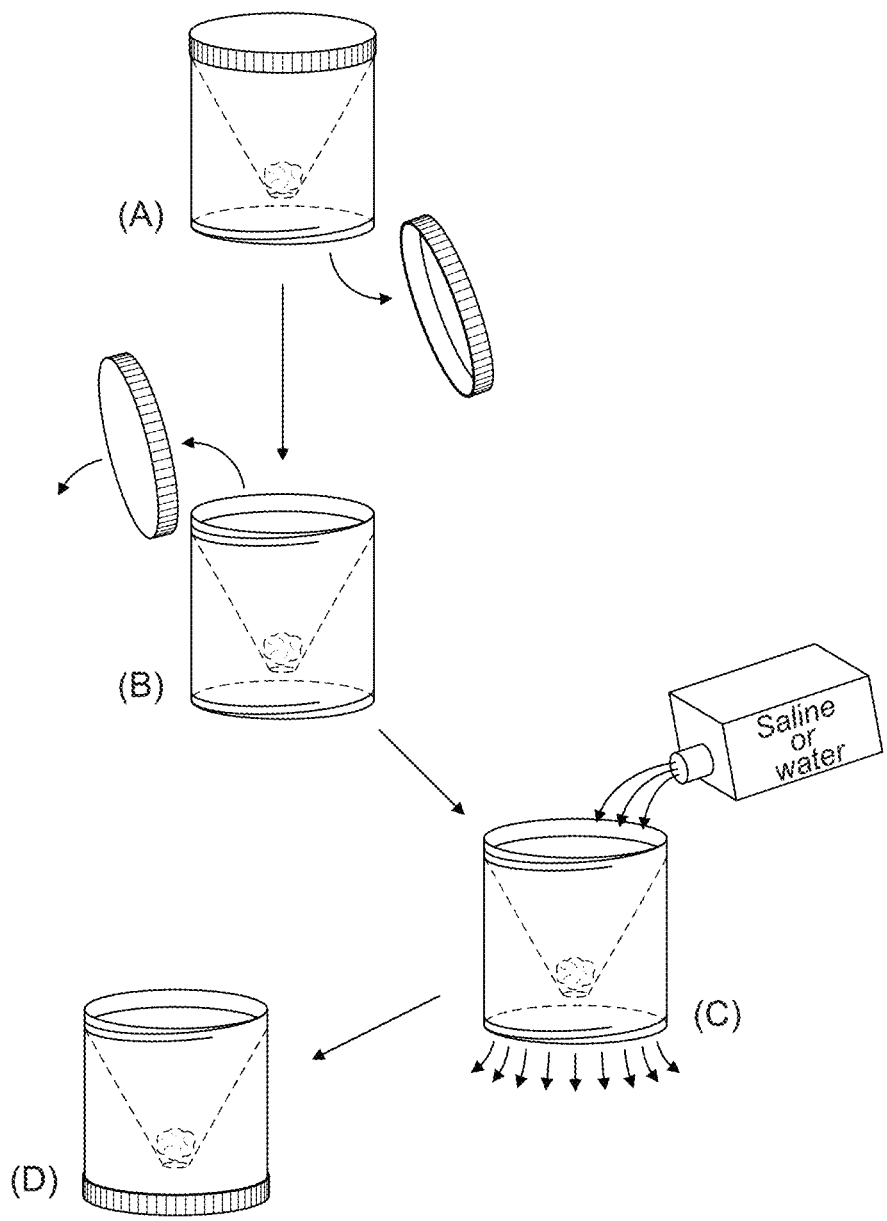
FIG. 14 discloses another embodiment of a sputum-washing method of the present invention.

FIG. 14 discloses a washing method using sputum-washer embodiments disclosed in FIGS. 11 and 12, after collection of the specimen as disclosed in FIG. 13. The sputum washing process in FIG. 14 starts with a removal of the top lid 94 and bottom lid 96. In the preferred embodiment, the bottom lid 96 is removed first and the top lid 94 is removed second (see illustrated steps (A) and (B) in FIG. 14). The order of these steps, however, could be reversed. If the device arrives with the grabber tool 8 inside the container, the tool is also removed. In the next step, a wash fluid, e.g., saline or tap water, is poured over the specimen for a predetermined duration (e.g., approximately 5 to 15 seconds) while gently swirling the sputum washer (see illustrated step (C) in FIG. 14). During this time, unlike in the sputum washer embodiment in FIGS. 1-8, in which the wash fluid is drained out of the decanting port and out of the opening at the top of the container. (see illustrations (D) and (E) in FIG. 10), in the method disclosed in FIG. 14, the wash fluid is being drained from the opening at the bottom of the container. Moreover, this draining is done simultaneously with washing/rinsing (decontaminating) the sputum specimen, as opposed to being done after agitation. As a result, the container 90 in the sputum washer embodiments of FIGS. 11 and 12 does not need to have a wash-fluid fill line.

Next, the bottom lid 96 is put back on the device and the specimen is sampled (see illustrated step (D) in FIG. 14). (It is, however, possible to sample the specimen without putting the bottom lid 96 back on.) The specimen can be sampled (removed) from the mesh for laboratory testing. The grabber tool 8 may be used to facilitate sampling using the grabber tool as shown in step (F) of FIG. 10. If the sputum-washer includes a sputum cutting feature, the feature may be used to cut (limit or downsize) the sample. Alternatively, sampling of the washed sputum specimen could proceed from the plate with a loop or pipet.

Once the washed specimen has been evaluated and/or sampled, it may be refrigerated for future testing. Depending on storage duration, the washing procedure may be repeated later. If the specimen is no longer needed, the sputum washer device should be discarded according to the CLIA-approved biohazardous disposal protocol.

Alternatively, in the sputum-washer embodiment using the top and bottom lids, a washing method would include the following steps: (a) remove the top lid; (b) fill the sputum-washer up to a fill line with a wash fluid; (c) replace the top lid; (d) tumble/roll (i.e., agitate) for a predetermined duration to expose the sputum bolus to the wash fluid, in order to dilute and dissolve the salivary contaminants from the specimen bolus: (e) leaving the top lid on, invert the sputum-washer; (f) remove the "bottom" lid, which is now at the top of the inverted device and decant (drain) the wash fluid from the device; (g) with the device in the inverted orientation, put the bottom lid back on (note, this step may be omitted); (h) invert the device again, to place it in the original orientation (i.e., the top lid is again at the top); (i) remove the top lid and sample the specimen from the mesh zone using a grabber tool.

While the foregoing descriptions disclose specific values, unless expressly stated otherwise, other specific values may be used to achieve similar results. Further, the various features of the foregoing embodiments may be selected and combined to produce numerous variations of improved systems. For example, the sputum washer embodiment disclosed in the FIGS. 1-8 may use the suction-top lid 101, disclosed in FIG. 12, during the sputum specimen collection process.

In the foregoing specification, exemplary embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings, and therefore the scope of the invention is to be limited only by the claims.

Moreover, in this document, relational terms such as first and second, and the like may be used solely to distinguish one entity or action from another entity or action without necessarily requiring or implying any actual relationship or order between such entities or actions. The terms "comprises", "comprising", "has", "having", "includes", "including", "contains", "containing" or any other variation thereof, are intended to cover a non-exclusive inclusion, such that a process, method, article, or apparatus that comprises, has, includes or contains a list of elements does not include only those elements but may include other elements not expressly listed or inherent to such process, method, article, or apparatus. An element preceded by "comprises . . . a", "has . . . a", "includes . . . a" or "contains . . . a" does not, without more constraints, preclude the existence of additional identical elements in the process, method, article, or apparatus that comprises, has, includes or contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly. A device or structure that is "configured" in a certain way is configured in at least that way but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Tus, the following claims are hereby incorporated into the Detailed Description, with each claim standing on its own as a separately claimed subject matter.

What is claimed is:

1. A specimen collection apparatus comprising:
   a) a container having a top end, a bottom end, a peripheral sidewall, and an opening at said top end;
   b) a mesh positioned within said container opening and above said bottom end, said mesh configured to support a sputum specimen and further configured to allow passage of a wash fluid;
   c) a flange supporting said mash and coupling the mesh to said peripheral sidewall, said flange having a decanting port located between said mesh and said peripheral sidewall; and
   d) a removable lid configured to seal said opening:
   wherein said flange and said removable lid are configured to form a barrier between said mesh and said decanting port, said barrier capable of blocking the sputum specimen from passing through it during washing of said sputum specimen.

2. The apparatus of claim 1, wherein said removable lid comprises a textured surface for manual gripping.

3. The apparatus of claim 1, wherein said removable lid is secured to said container via a threaded connection.

4. The apparatus of claim 1, wherein a lower surface of said removable lid comprises a first circumferential rib, and wherein said barrier is created when said first circumferential rib presses against said flange.

5. The apparatus of claim 4, wherein said lower surface of said removable lid comprises a second circumferential rib having a larger diameter than said first circumferential rib, said second circumferential rib configured to enhance sealing of said container when pressed against said flange.

6. The apparatus of claim 1, wherein said flange further comprises an overhang above said mesh, said overhang configured to prevent discarding of the sputum specimen during draining of the wash fluid via said decanting port and out of said container opening.

7. The apparatus of claim 6, wherein an edge of said overhang has a profile that facilitates cutting of the sputum specimen during specimen sampling.

8. The apparatus of claim 7, wherein said profile includes a groove that facilitates cutting of the sputum specimen during specimen sampling.

9. The apparatus of claim 1, further comprising a grabber tool to facilitate specimen sampling.

10. The apparatus of claim 9, wherein said grabber tool is configured for stowing in said decanting port.

11. The apparatus of claim 1, wherein said mesh is cone-shaped, and wherein said cone-shaped mesh comprises a sampling loop plate on the bottom.

12. The apparatus of claim 1, wherein said peripheral sidewall includes a wash-fluid fill line.

13. A specimen collection method comprising the steps of:
 providing an apparatus comprising i) a container having a top end, a bottom end, a peripheral sidewall, and an opening at said top end; ii) a mesh positioned within said opening and above said bottom end, said mesh configured to retain a sputum specimen and further configured to allow passage of a wash fluid; iii) a flange supporting said mesh and coupling the mesh to said peripheral sidewall, said flange having a decanting port located between said mesh and said peripheral sidewall; and iv) a removable lid;
 depositing the sputum specimen on said mesh:
 sealing said container using said removable lid, wherein said flange and said removable lid cooperate to form a barrier between said mesh and said decanting port, said barrier capable of blocking the sputum specimen from passing through it;
 agitating the sputum specimen in the presence of the wash fluid to remove a contaminant from the sputum specimen;
 unsealing said container; and
 draining the wash fluid from said container via said decanting port and out of said container opening.

14. The method of claim 13, further comprising the step of using a grabber tool to manually remove at least a portion of the sputum specimen from said container.

15. The method of claim 14, further comprising a step of cutting the sputum specimen during removal of the at least a portion of the sputum specimen from said container.

16. The method of claim 14, further comprising a step of removing said grabbing tool from a stowed position inside said container.

17. The method of claim 13, further comprising a step of pouring the wash fluid into said container up to a fill line located on said peripheral sidewall of said container.

18. The method of claim 13, further comprising a step of removing said lid off said container.

19. The method of claim 13, wherein said agitating step is performed for a duration from about 5 seconds to about 15 seconds.

* * * * *